(12) United States Patent
Birgy et al.

(10) Patent No.: US 7,763,867 B2
(45) Date of Patent: Jul. 27, 2010

(54) PARTICLE THERAPY SYSTEM, METHOD AND DEVICE FOR REQUESTING A PARTICLE BEAM

(75) Inventors: Denis Birgy, Grossenseebach (DE); Harald Breuninger, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 920 days.

(21) Appl. No.: 11/520,874

(22) Filed: Sep. 13, 2006

(65) Prior Publication Data

US 2007/0114471 A1    May 24, 2007

Related U.S. Application Data

(60) Provisional application No. 60/717,834, filed on Sep. 16, 2005.

(30) Foreign Application Priority Data

Sep. 16, 2005    (DE) .................... 10 2005 044 408

(51) Int. Cl.
*G21G 1/00*    (2006.01)
(52) U.S. Cl. .................... 250/492.3; 250/398
(58) Field of Classification Search ........... 250/492.3, 250/398, 492.1; 378/65
See application file for complete search history.

(56) References Cited

U.S. PATENT DOCUMENTS

| | | | |
|---|---|---|---|
| 5,260,581 A | 11/1993 | Lesyna et al. | |
| 5,895,926 A | 4/1999 | Britton et al. | |
| 7,012,267 B2 * | 3/2006 | Moriyama et al. | ....... 250/492.3 |
| 7,173,264 B2 * | 2/2007 | Moriyama et al. | ....... 250/492.3 |
| 2004/0200982 A1 | 10/2004 | Moriyama et al. | |
| 2005/0029472 A1 | 2/2005 | Ueno et al. | |
| 2006/0022152 A1 | 2/2006 | Natori et al. | |

FOREIGN PATENT DOCUMENTS

| | | |
|---|---|---|
| DE | 10 2004 027 071 A1 | 1/2006 |
| EP | 0 986 070 A1 | 3/2000 |
| EP | 1 454 657 A2 | 9/2004 |

OTHER PUBLICATIONS

H. Blattmann, "Beam Delivery Systems for Charged Particles", Radiat. Environ. Biophys., (1992), 31: pp. 219-231.
German Office Action dated Apr. 10, 2008 for EP 0612 0101.8-2319 with English translation.

* cited by examiner

*Primary Examiner*—Kiet T Nguyen
(74) *Attorney, Agent, or Firm*—Brinks, Hofer, Gilson & Lione

(57) ABSTRACT

A particle therapy system, method and device for requesting a particle beam is provided. The particle therapy system includes an accelerator that accelerates particles; a particle beam directing unit that directs particles to at least one irradiation location; and an assignment unit that assigns and monitors the correct particle beam direction. At least one of the irradiation locations has a control unit connected via a first link to the assignment unit and is operable to request a particle beam for an irradiating operation, so that the presence of the request signal at a signal input of the assignment unit establishes the requesting irradiation location.

13 Claims, 2 Drawing Sheets

PARTICLE THERAPY SYSTEM, METHOD AND DEVICE FOR REQUESTING A PARTICLE BEAM

The present patent document claims the benefit of the filing date under 35 U.S.C. §119(e) of Provisional U.S. Patent Application Ser. No. 60/717,834 filed on Sep. 16, 2005, which is hereby incorporated by reference. This application also claims the benefit of DE 10 2005 044 408.3, filed Sep. 16, 2005.

The present embodiments relate to a particle therapy system, method and device for requesting a particle beam.

Generally, a particle therapy system includes a particle accelerator unit, an adjoining particle beam directing unit, and a plurality of irradiation locations. The particles, for instance protons, pions, or helium, carbon, or oxygen ions, are accelerated using, for example, a synchrotron or cyclotron. The accelerated high-energy particles are decoupled from the particle accelerator unit and coupled into the particle beam directing unit, referred to also as a high-energy beam transport system (HEBT). In the case of a synchrotron, decoupling takes place via, for instance, a knock-out exciter. The HEBT directs the high-energy particles to an irradiation location. The irradiation location is the area where an irradiating operation is performed.

For example, during tumor therapy, a patient is positioned in the particle beam path and the high-energy particles are directed at the patient's tumor. An irradiation location is referred to below also as a treatment location. A distinction is made between "fixed beam" treatment chamber and "gantry-based" treatment chamber. A fixed beam treatment chamber has particles that impinge upon a treatment location from a fixed direction. In the gantry-based treatment chamber the particle beam is directed onto the treatment location of the gantry from different directions. The beam quality is monitored at an irradiation location referred to below as a checking location. Beam parameters such as particle energy, energy distribution, and beam intensity are monitored at the checking location by means of quality measurements.

Stringent demands are placed on the safety of a particle therapy system. For example, the particle beam must only be directed to an irradiation location that is prepared for an irradiating operation and has requested the particle beam. The particle beam must also have the correct requested parameters. Fast interruption of particle routing is also necessary in an emergency, for example, the HEBT has a baffle allowing the particle beam to be quickly switched off. Conventionally, a control and security system of the particle therapy system insures that a particle beam characterized by the requisite parameters is in each case routed into the relevant treatment chamber.

The requisite parameters are defined by a treatment plan (therapy plan). The treatment plan indicates how many particles are to impinge upon the patient, from which direction and with what energy. The particles' energy determines the depth of penetration into the patient. The site at which maximum interaction with the tissue takes place during particle therapy is the site where the maximum dose is applied. The parameters required by the treatment plan are converted by an accelerator control unit into setting parameters. The setting parameters are in the form of, for example, machine parameters for the accelerator and particle beam directing unit. The information indicating the irradiation location to which the particle beam is to be routed is converted into setting parameters for the particle beam directing unit. A control unit of the irradiation location controls, for example, a positioning device by means of which a patient to be irradiated is positioned relative to the particle beam.

A particle therapy system having a plurality of fixed beam treatment locations and a gantry is disclosed in EP 0 986 070. Various irradiation systems and techniques have been described by H. Blattmann in "Beam delivery systems for charged particles", Radiat. Environ. Biophys. (1992) 31:219-231.

A method for selecting a treatment room is disclosed in U.S. Pat. No. 5,260,581. A control and security system for a radiation beam treatment facility is disclosed in U.S. Pat. No. 5,895,926.

SUMMARY

The present embodiments are directed to a particle therapy system, method and device for requesting a particle beam, which may obviate one or more of the problems due to the limitations and disadvantages of the related art.

In one exemplary embodiment, a particle therapy system includes an accelerator that accelerates particles; a particle beam directing unit that directs particles to at least one irradiation location; and an assignment unit that assigns and monitors the correct particle beam direction. At least one of the irradiation locations has a control unit connected via a first link to the assignment unit and is operable to request a particle beam for an irradiating operation, so that the presence of the request signal at a signal input of the assignment unit establishes the requesting irradiation location.

In another exemplary embodiment, the first link is a direct and permanently assigned signal link, for example, a direct hardware link. For example, the signal link is a single and safety-oriented signal lead. A clamping of a plurality of cable sections, with a single, continuously laid cable is used.

A direct and permanently assigned signal link provides a unique assignment of an irradiation location to a signal input. The correct irradiation location will be recognized by the assignment unit without the need here for confirmation via, for example, a protocol to verify the correct irradiation location. The conventional additional verification step is eliminated. A hardware-coded and controlled procedure allows secured directing of a particle beam along a particle path to the requesting irradiation location. In one exemplary embodiment, the signal link is used in one direction, so there will be no need for fault-prone logic that differentiates the direction of signal transmission.

Conventionally, a method, as described in U.S. Pat. No. 5,895,926, used a pure bus solution onto which variable signaling can be imposed. Hardware coding permits a secured assignment and/or secured beam availability check using dedicated hardware signal leads that will curb manipulation opportunities.

In one exemplary embodiment, a particle therapy system has an accelerator and particle beam directing unit for accelerating particles and for routing particles from the accelerator to at least two irradiation locations. The accelerator unit is, for example, a cyclotron or a synchrotron, into which possibly pre-accelerated particles are coupled. The particle beam is directed with the aid of, for example, at least one settable element in the beam path. The element or elements is/are set with the aid of an accelerator control unit according to a beam path. Setting parameters needed for setting are conveyed and stored in, for example, a buffer.

The particle therapy system further includes an assignment unit that assigns and monitors correct particle beam routing along the beam path. The particle beam is directed within the accelerator and particle beam directing unit to an irradiation location requesting the particle beam. The assignment unit is, for example, a safety-oriented controlling unit that can be controlled utilizing a stored-program.

At least one of the treatment locations has a control unit that is directly connected via, for example, a direct and permanently assigned signal link to a signal input of the assignment unit and is operable to request a particle beam for an irradiating operation over the signal link, so that the presence of the request signal at the signal input will uniquely establish the requesting irradiation location.

In one exemplary embodiment a second link is provided between the assignment unit and control unit of the irradiation location that conveys a confirmation signal from a signal output of the assignment unit to the control unit.

In another exemplary embodiment, the therapy system has a plurality of irradiation locations. These are each directly connected via a signal link to in each case one signal input (and possibly one signal output) of the assignment unit. The connections are separate from one another. The control units are connected via a direct hardware link to the assignment unit by, for example, individual, direct signal leads.

In one exemplary embodiment, the accelerator and particle beam unit have a plurality of elements. These elements are, for example, likewise each directly connected via in each case one permanently assigned signal link to in each case one signal output of the assignment unit. The connections are separate from one another. The settable elements are connected via a direct hardware link to the assignment unit by, for example, individual, direct signal leads.

Examples of settable elements are beam-bending magnets that deflect the particle beam from the beam-directing system into the individual treatment rooms, a beam decoupling device of an accelerator, for example a knock-out exciter of a synchrotron ring, and a dipole magnet of a baffle in the HEBT. Possible setting parameters are, for example, the magnetic field being applied, a current value required to be set, and a HF decoupling frequency. In one exemplary embodiment, a settable element is operable to process and, as a function of the presence of the activation signal, implement the at least one conveyed setting parameter. The settable element has a buffer, for example, in which a conveyed setting parameter can be stored and from which it can be read out after the activation signal has been received.

The setting parameters are conveyed via, for example, a data bus system to which the accelerator control unit and respective elements are linked. In one exemplary embodiment, the setting parameter is determined by the irradiating operation taking place at the irradiation location.

In one exemplary embodiment, one control unit of the irradiation locations is linked to the data bus system or to a data bus system of its own for exchanging required parameters of the particle beam and/or parameters of the accelerator and particle beam directing unit.

Examples of irradiation locations are a treatment location for radiation beam therapy, for example a fixed-beam or gantry treatment location, and a checking location for checking parameters on which particle irradiating is based.

In one exemplary embodiment, a method for requesting a particle beam comprises, sending a request signal from one of the irradiation locations to the assignment unit over a direct and fixed assigned signal link. A beam path, which routes particles to the requesting irradiation location, in the particle therapy system is then set.

DETAILED DESCRIPTION

Figure 1:
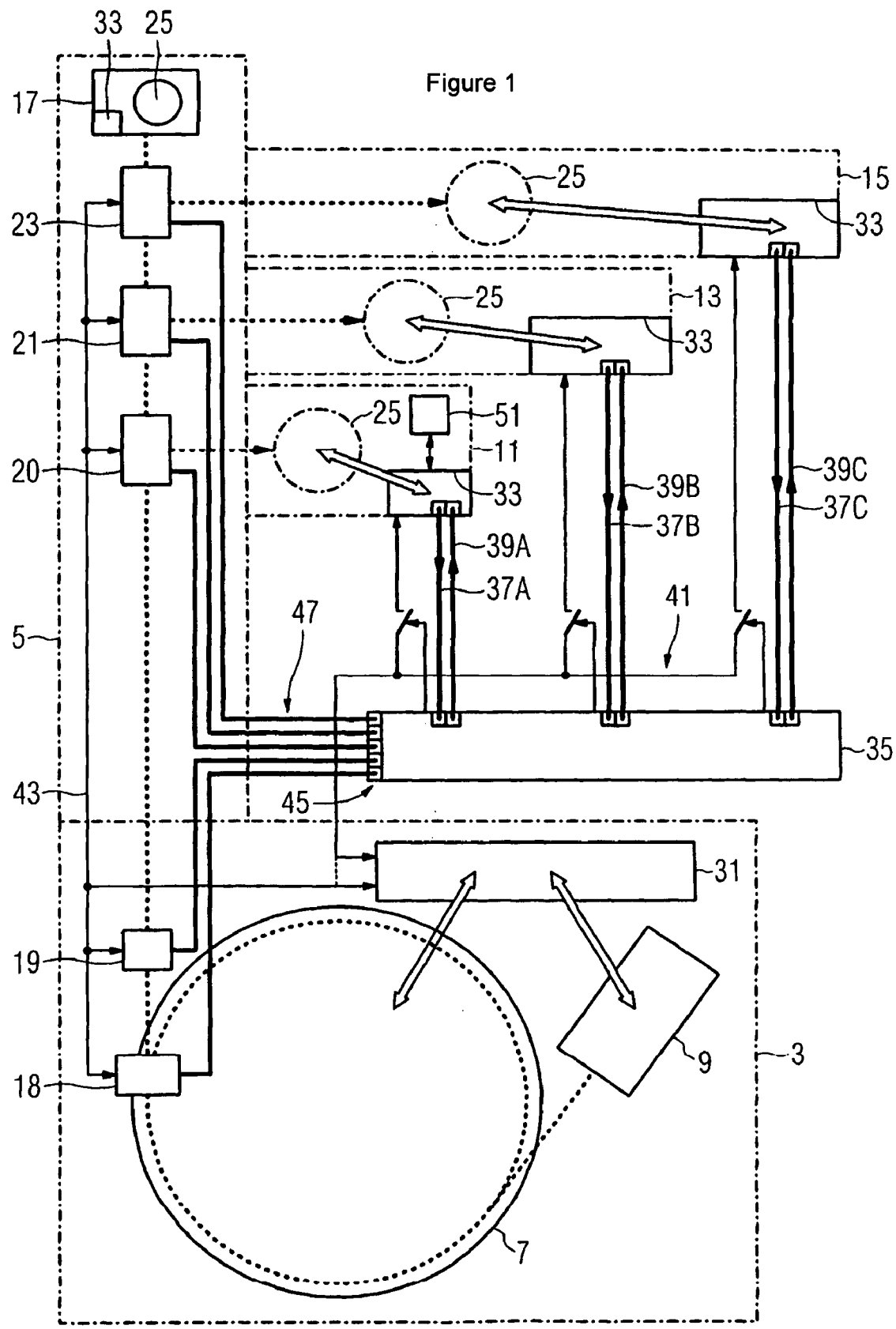
FIG. 1 illustrates an exemplary therapy system.

FIG. 1 illustrates an exemplary therapy system 1 and the interaction between different control units. The control units effect and monitor the setting of components that direct a beam having appropriate parameters to an irradiation location. Important signals are conveyed over a non-fault-prone hardware link. The hardware link includes a specific, separate lead and has been uniquely assigned to the transmission of a signal.

In one exemplary embodiment, as shown in FIG. 1, the therapy system 1 includes an accelerator unit 3 and a particle beam directing unit 5. A synchrotron 7 having an upstream linear accelerator unit 9 exemplifies an accelerator. The beam directing unit 5 distributes the particles among a plurality of irradiation locations. For example, the particles are directed to treatment locations 11, 13, and 15 for radiation beam therapy and a checking device 17 that insures the particle beam's quality. The checking device 17 checks the quality of the particle beam with the aid of quality procedures. The quality procedures use regular tests to verify the previously defined beam parameters, for example, position and intensity graduation of particle energy. The intensity graduation is contained in, for example, a library and is checked by automated Bragg peak measurements performed on phantoms.

Particles stored in, for example, the synchrotron ring 7 are decoupled with the aid of a decoupling device 18 and directed into the beam directing unit 5. In one exemplary embodiment, an installed baffle 19 includes three small dipole magnets located behind the extraction unit 18. The baffle 19 is operable to quickly switch off the beam when the irradiating operation has finished or is interrupted. Quickly switching off, for example, the central dipole will cause the beam to be destroyed on a collimator.

The particles are directed to the irradiation locations 11, 13, and 15 by deflecting the particle beam, using bending magnets 20, 21, and 23, from a main beam direction in the beam directing unit 5. The checking device 17 is located in the main beam direction. Interaction between the particles and a patient to be irradiated or a phantom takes place at the irradiation locations in irradiation zones 25. In one exemplary embodiment, one of the irradiation zones 25 is a maximally scannable scanning area of a (raster) scanning device. Alternatively, the irradiation zones 25 are, for example, but not limited to, a maximally irradiable scatter area of a scatter device, or a settable gantry irradiation area.

In one exemplary embodiment, the linear accelerator unit 9 includes one or more operable ion sources, a low-energy beam guide, a radio-frequency quadrupole, a drift tube accelerator, and an injection beam guide. linear accelerator unit 9, for example, produces one or more particle types and frees the particle types from contamination by undesired particle types. The linear accelerator unit 9 also sets the beam intensity in the low-energy range for the synchrotron, for example, pre-accelerates the particles. The linear accelerator unit 9 prepares the particle beam in terms of, for example, pulse length and beam parameters in keeping with the synchrotron's requirements.

In one exemplary embodiment, if a scanning method is employed during the use of the therapy system 1, a slow beam extraction will facilitate optimal use of the accelerated particles and precise beam monitoring while a tumor is being scanned. In this embodiment, for example, if a synchrotron is used, then beam extraction can utilize a HF knock-out method with a knock-out exciter that forms the decoupling unit 18. In this embodiment, for example, the control and security system of the therapy system 1 is split into several components. Alternatively, provided the different aspects are taken into account during monitoring, splitting can be different or there can be no splitting involved.

In the exemplary embodiment according to FIG. 1, an accelerator control unit 31 insures that the requested particle beam will arrive in the treatment room in keeping with its specification. Control units 33 located at the irradiation locations control the flow of an irradiating operation and insure that the particle beam will impinge upon a patient according to the treatment plan.

The control and security system further includes an assignment unit 35. The assignment unit 35 assigns a particle beam to the irradiation location 11, 13, 15 that has requested it. This assignment insures that a particle beam will be directed only to the irradiation location 11, 13, 15 that has requested it. The assignment unit 35 is connected to the control units 33 to convey a request signal over a fixed and uniquely assigned signal lead 37A, 37B, 37C. There can be a further permanently assigned signal lead 39A, 39B, 39C between the assignment unit 35 and control units 33 to convey for example, a confirmation signal from the assignment unit 35 to the irradiation location to which the particle beam is directed next.

In one exemplary embodiment, the control and security system has at least one data bus system 41 to which the control units 33 and accelerator control unit 31 are linked. Said data bus system conveys setting parameters to the accelerator unit 3 and particle beam directing unit 5 for an irradiating operation that is to be performed next. The assignment unit 35 influences the data bus system 41, so that only the irradiation location 11, 13, 15 that has received a confirmation signal is able to convey parameters.

In one exemplary embodiment, the accelerator control unit 31 is linked to a data bus system 43 (dashed link). In an alternate embodiment, the data bus system is combined with the data bus 41. The accelerator control unit 31 and elements are operable to be set using the accelerator and beam directing unit linked to the data bus system 43. In the exemplary embodiment according to FIG. 1 the decoupling unit 18, the baffle 19, and the bending magnets 20, 21, 23 are linked to the data bus system 43. For example, specific setting parameters needed by the elements for setting the currently requested particle beam path and for transporting the particles with the correct energy are conveyed to the elements via the data bus system 43. The specific setting parameters of the elements in the high-energy beam path are determined as a function of a specified irradiation location.

In one exemplary embodiment, the specific setting parameters are implemented only if an activation signal of the assignment unit 35 is present at the element to be set. The elements to be set are connected to signal outputs 45 of the signal assignment unit 35 via direct, permanently assigned signal leads 47.

In one exemplary embodiment, request and/or activation signals are sent and received via specific unambiguous hardware links. It is not possible to send signals from other irradiation locations or conveyed to other elements erroneously. Thus, certain and known irradiation locations and/or explicitly activated elements will be set to establish the beam path.

A therapy plan 51 establishes the irradiating operation using all the plan's requisite parameters, for example, direction of beam incidence, beam intensity, particle type, or particle energy.

For example, when the treatment plan for the patient has been loaded at the irradiation location 11, 13, 15, all safety requirements have been met, and the patient has been suitably positioned, a therapy control system, for example, a control unit 33 of the irradiation locations 1113, 15, requests a beam having the specific parameters for the current irradiation location. Only tested and released datasets of parameters that are stored in the accelerator control system 31 can be used and requested.

In one exemplary embodiment, an operator initiates sending of a request signal from the control unit 33 of the irradiation location 11 along the assigned signal lead 37A to the assignment unit 35. The assignment unit 35 checks the availability of the particle beam. If another irradiating operation is taking place at an adjacent irradiation location 13, 15, then the assignment unit 35 will not assign the requesting treatment room the particle beam until said irradiating operation has finished. When the adjacent irradiation location 13, 15 is complete, the assignment unit 35 releases the connection from the control unit 33 of the treatment room 11 to the accelerator control unit 31 in the data bus system 41 that conveys the desired parameters of the ensuing irradiating operation.

In one exemplary embodiment, the assignment unit 35 sends activation signals, over the assigned signal leads 47, to the settable elements, for example, the decoupling unit 18, the baffle 19, and the bending magnet 20, needed for beam routing to the requesting irradiation location. The accelerator control unit 31 conveys specific parameters to the elements. The setting parameters are conveyed by the accelerator control unit 31 to be implemented in the elements and establish the particle beam path needed, only if the activation signal is present. In one exemplary embodiment, priority is given to deactivating the settable elements. Corresponding currents will be set only if an activation signal is present. Deactivation, for example, is the default of the "current to zero" is set. To convey an activation signal, a signal output of the assignment unit 35 is connected via a direct and permanently assigned signal link to at least one of the settable elements.

In another exemplary embodiment, a setting parameter is implemented in the element in an interaction with the activation signal. In one exemplary embodiment, the activation signal must be present before and/or during implementation. Priority is given to deactivating the settable elements. For example, the accelerator control unit 31 acts as a locking mechanism. Corresponding currents will be set if an activation signal is present. Deactivation means that, for example, the defaults have been set and there is no flow of current in the magnet coils.

In one exemplary embodiment, after the elements are set, the assignment unit 35 conveys a confirmation signal along the direct connection lead 39A. Irradiation particles are directed to the treatment area 25 when the confirmation signal has been confirmed by the treatment location 11.

The sequence of setting and signal-conveying operations is flexible, for example, is not limited to the presence of an activation signal for the actual implementation of physical settings. Alternatively, the confirmation signal can, for example, be conveyed to the treatment room 11 along the connection lead 39A directly after the particle beam has been assigned to the treatment room 11. In one exemplary embodiment, a "beam on" signal actively initiated on the part of the control unit 33 of the treatment room in response to the confirmation signal will give rise to activation signals from the accelerator control unit 31 to the relevant elements. The setting parameters are physically implemented in the elements and the particles directed to the irradiation location. In this embodiment, implementing will only take place once the confirmation signal has been received and an incorrect setting can be avoided. For example, when a non-requesting control unit 33 receives a confirmation signal, deactivation will be performed automatically.

In this embodiment, the procedure can be divided into three stages. In a preparatory stage, only the control unit 33 and assignment unit 35 communicate (beam requesting signal, beam assignment confirmation signal, and "beam on" signal). In a setting stage, the assigned control unit and accelerator control unit 31 communicate. For example, the relevant beam parameters are requested and the relevant parameters are conveyed to the elements and accelerator unit. In an activation stage, the assignment unit 35 communicates with the elements and sets the elements so that the parameters conveyed by the accelerator control unit 31 are implemented. The activation stage makes setting the elements physically possible and implements the setting; it can even take place at the same time as the setting stage.

In one exemplary embodiment, the therapy system 1 operates autonomously during the irradiating operation. For example, the control unit 33 controls scanner magnets and beam diagnosing units that monitor the beam quality. The operating personnel's only possibility of intervention is to terminate the irradiating operation. If beam termination is initiated, or in the event of a fault in the system detected elsewhere, then via the direct and permanently assigned signal leads to the settable elements the assignment unit 35 will withdraw permission to be activated. For example, the occurrence of a fault will cause the particle beam to be destroyed within the baffle 19 through a reduction in a dipole magnet field. The bending magnets 20, 21, 23, for example, will additionally be de-energized and the KO exciter switched off.

On completion of an irradiating operation the settable elements can be re-set to their defaults. For example, the bending magnets 20, 21, 23 and/or baffle 19 magnet fields will be reduced to zero and the KO frequency switched off. In reciprocal action with a utilization-optimizing operating system of the therapy system 1 that controls irradiating operations that arise, a default, relating possibly to the irradiating operation to be performed next, can be skipped by appropriately controlling the assignment unit 35 so that the beam path will be available for the succeeding irradiating operation.

The functions of the various components of the control and security system for requesting the beam and establishing the beam path can be summarized thus:

The accelerator control unit 31 checks the correct values of the setting parameters for the settable elements in the accelerator and beam directing unit.

The assignment unit 35 insures the settability of said parameters by means of an activation process during which only the specific elements needed for a beam path are selectively activated. For that purpose the assignment unit preferably has a table having the possible beam paths stored in, for example, a look-up table. A check is additionally carried out on the particle beam's availability within the assignment unit 35 preferably embodied as a safety-oriented controlling unit that can be stored-program controlled. The particle beam will only be assigned if available.

The control units 33 at the irradiation locations supply the data from the irradiation plan and finally decide on the directing of the beam, which is to say they initiate beam directing to the relevant irradiation location.

Use of the direct and permanently assigned links is not restricted to the embodiment outlined in FIG. 1. The link between one of the control units 33 and the assignment unit 35 can be embodied in an alternative way. For example, the control units 33 and the assignment unit 35 can be connected via an antenna receiver/transmitter.

The illustrated distribution is exemplary only. For example, different elements can be combined within one unit. In one exemplary embodiment, parameters for the therapy plan can be directed to the accelerator control unit 31 directly and not via a control unit 33 of a treatment chamber.

Figure 2:
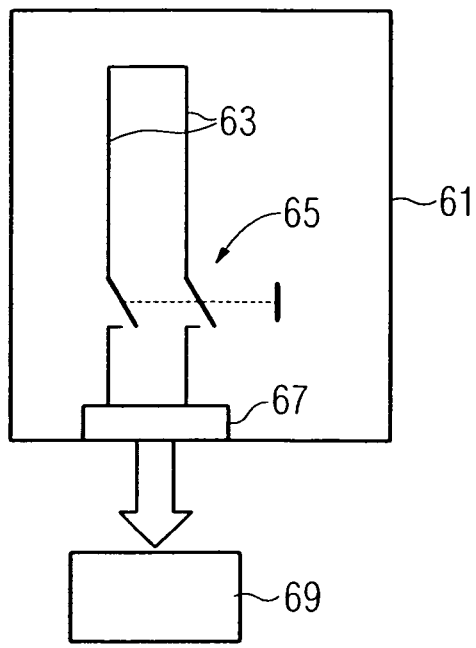
FIG. 2 is a schematic of a safety-oriented switch unit according to one exemplary embodiment.

FIG. 2 illustrates an exemplary switch unit 61. The switch unit 61 can be used in, for example, the control unit 33 and/or the assignment unit 35. The switch unit 61 is used to convey a request signal, confirmation signal, and/or activation signal. In one exemplary embodiment, two leads 63 are connected in parallel. The two leads 63 are connected via a positive-opening/positive-closing switch 65 to a signal output 67. The switch 65 opens/closes the two leads 63 together and, in the event of a fault, assumes a safe state. The signal output is connected to a unit 69. For example, the unit 69 is one of the control units 33, the assignment unit 35, the decoupling unit 18, the baffle 19, or one of the bending magnets 20, 21, 23.

Figure 3:
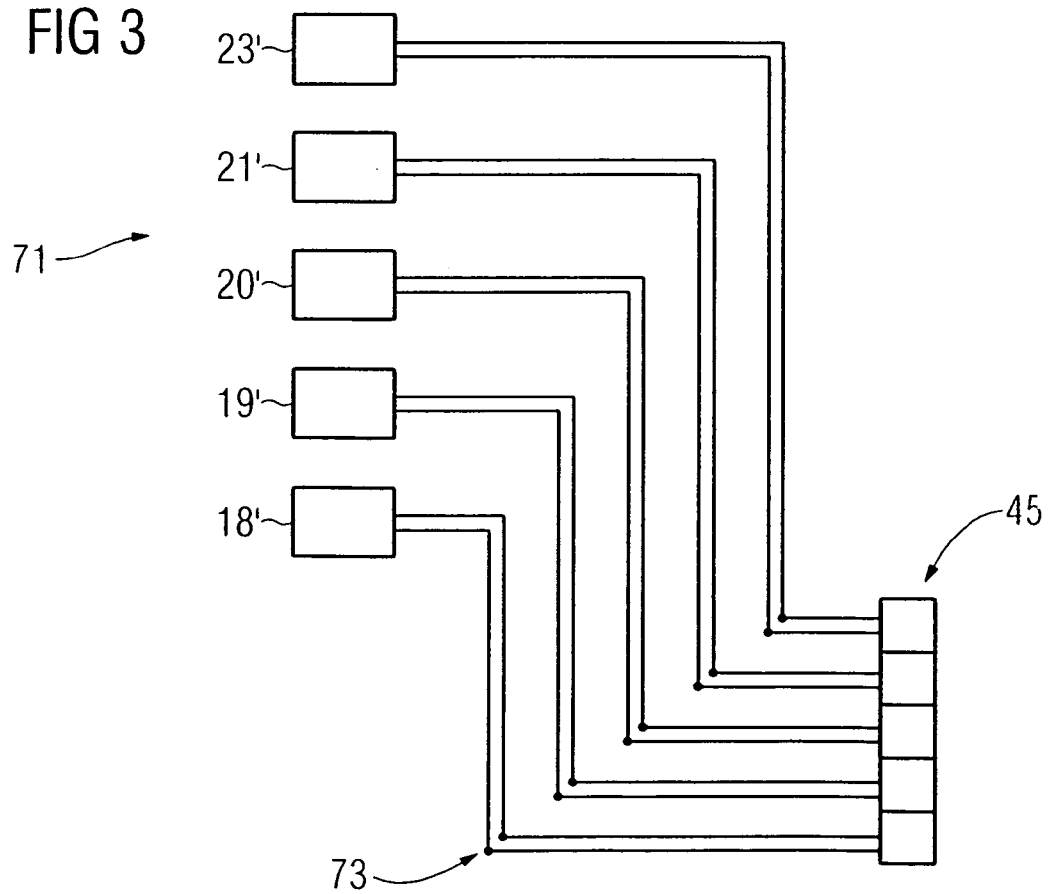
FIG. 3 illustrates safety-oriented links according to one exemplary embodiment.

FIG. 3 illustrates the use of double leads for conveying activation signals to elements 71, for example, a decoupling unit 18', a baffle 19', and bending magnets 20', 21', 23'. The leads are applied by a corresponding switch unit to signal outputs 45' which, according to FIG. 1, are part of the assignment unit 35. The use of clamping means 73 may in view of the size of a therapy system be unavoidable.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A particle therapy system having:
   an accelerator that accelerates particles;
   a particle beam directing unit that is operable to route the particles to at least one irradiation location; and
   an assignment unit that assigns and monitors a particle beam direction,
   wherein at least one of the irradiation locations has a control unit connected via a first link to the assignment unit and is operable to request a particle beam for an irradiating operation via the first link, and
   wherein the first link is connected only between the control unit and assignment unit, so that the presence of the request signal at a signal input of the assignment unit establishes the requesting irradiation location.

2. The particle therapy system as claimed in claim 1, wherein a second link is provided between the assignment unit and control unit of the irradiation location that conveys a confirmation signal from a signal output of the assignment unit to the control unit.

3. The particle therapy system as claimed in claim 2, wherein at least one of the signal links is a direct hardware link.

4. The particle therapy system as claimed in claim 3, wherein at least one irradiation location includes a control unit directly connected to a signal input of the assignment unit.

5. The particle therapy system as claimed in claim 4, wherein at least two control units are directly connected to at least one signal output of the assignment unit.

6. The particle therapy system as claimed in claim 5, wherein the assignment unit and the at least one control unit are linked to a data bus system that conveys a confirmation signal.

7. The particle therapy system as claimed in claim 6, wherein an accelerator control unit and the at least one control unit are linked to a data bus system that exchange parameters of the particle beam or parameters of the accelerator and particle beam directing unit, and wherein the parameters are established by the control system based on a therapy plan.

8. The particle therapy as claimed in claim 2, wherein the second link is a direct and permanently assigned link.

9. The particle therapy system as claimed in claim 3, wherein at least one of the signal links is a single signal lead.

10. The particle therapy system as claimed in claim 1, wherein the at least one of the irradiation locations is a treatment location where a patient is being irradiated with the particles.

11. The particle therapy system as claimed in claim 1, wherein the at least one of the irradiation locations is a checking device that checks parameters characterizing the particle irradiation operation.

12. The particle therapy system as claimed in claim 1, wherein the assignment unit has a controlling unit that is controlled by a stored program.

13. The particle therapy as claimed in claim 1, wherein the first link is a direct and permanently assigned link

* * * * *